(12) United States Patent
Bonnadier

(10) Patent No.: US 9,968,367 B2
(45) Date of Patent: May 15, 2018

(54) ORTHOPEDIC TOOL MADE OF A PLASTIC MATERIAL

(71) Applicant: Solvay Advanced Polymers, L.L.C., Alpharetta, GA (US)

(72) Inventor: Jean-Baptiste Bonnadier, Brussels (BE)

(73) Assignee: SOLVAY SPECIALTY POLYMERS USA, L.L.C., Alpharetta, GA (US)

(*) Notice: Subject to any disclaimer, the term of this patent is extended or adjusted under 35 U.S.C. 154(b) by 0 days. days.

(21) Appl. No.: 15/200,745

(22) Filed: Jul. 1, 2016

(65) Prior Publication Data

US 2016/0310150 A1    Oct. 27, 2016

Related U.S. Application Data

(63) Continuation of application No. 12/520,790, filed as application No. PCT/EP2007/064426 on Dec. 21, 2007, now abandoned.

(60) Provisional application No. 60/871,840, filed on Dec. 26, 2006.

(51) Int. Cl.
*A61B 17/16* (2006.01)
*A61B 17/00* (2006.01)

(52) U.S. Cl.
CPC ...... *A61B 17/1659* (2013.01); *A61B 17/1664* (2013.01); *A61B 17/1675* (2013.01); *A61B 2017/00955* (2013.01); *A61B 2017/00964* (2013.01)

(58) Field of Classification Search
CPC ................ A61B 17/1659; A61B 17/1664
See application file for complete search history.

(56) References Cited

U.S. PATENT DOCUMENTS

| | | | |
|---|---|---|---|
| 4,305,865 A | 12/1981 | Okada et al. |
| 4,604,097 A | 8/1986 | Graves et al. |
| 5,454,815 A | 10/1995 | Geisser et al. |
| 5,839,897 A | 11/1998 | Bordes |
| 5,994,445 A | 11/1999 | Kaschel et al. |
| 7,160,298 B2 | 1/2007 | Lawes et al. |
| 7,960,014 B2 | 6/2011 | Bushelman et al. |
| 2003/0220689 A1 | 11/2003 | Ritland et al. |

(Continued)

FOREIGN PATENT DOCUMENTS

| | | |
|---|---|---|
| DE | 10122387 | 10/2002 |
| EP | 574701 | 12/1993 |

(Continued)

OTHER PUBLICATIONS

USP Class VI, "Biological reactivity tests, in vivo," The United States Pharmacopeia Twenty-Ninth revision, The National Formulary Twenty-Fourth Edition, Jan. 1, 2006, pp. 2526-2530 (6 pp).

(Continued)

*Primary Examiner* — Nicholas Woodall
(74) *Attorney, Agent, or Firm* — Jarrod N. Raphael; Nikhil Patel

(57) ABSTRACT

The present invention relates to an orthopedic tool made of plastic material (M) comprising at least one semi-aromatic polyamide (P) comprising more than 50 mole % of recurring units obtained by the polycondensation reaction between at least one aliphatic diacid or derivative thereof and at least one aromatic diamine. In particular, hip rasp consisting essentially of at least one plastic material comprising at least one PMXDA polymer.

6 Claims, 2 Drawing Sheets

(56) References Cited

U.S. PATENT DOCUMENTS

Figure 1:
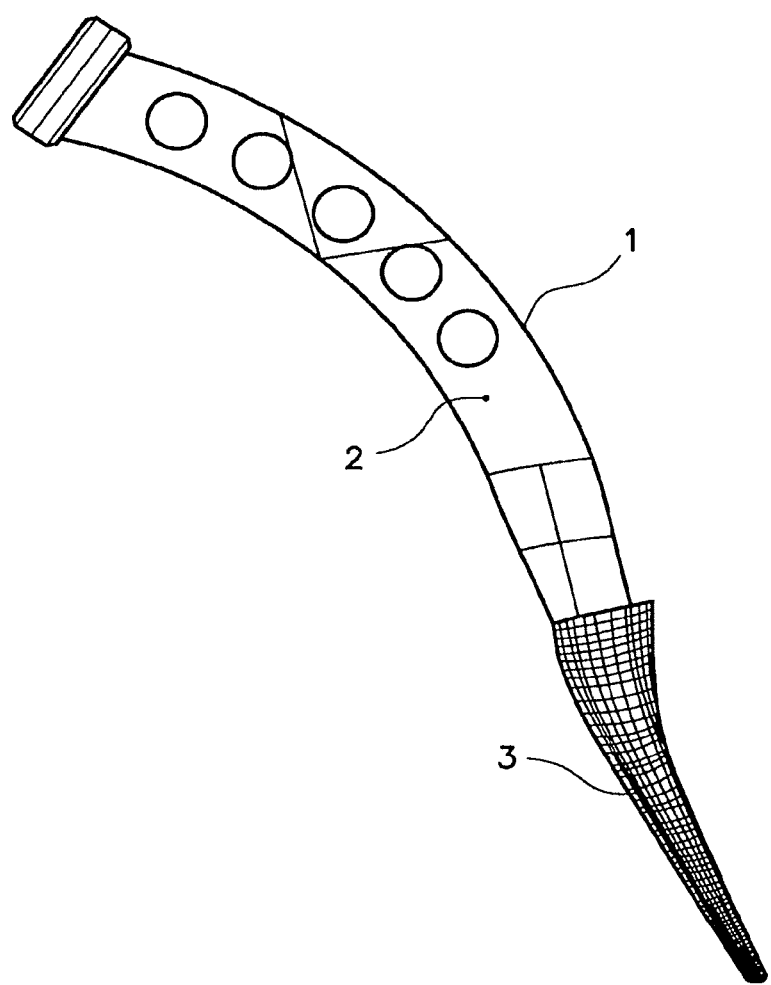

| | | |
|---|---|---|
| 2006/0030854 A1 | 2/2006 | Haines |
| 2006/0111725 A1 | 5/2006 | Biegun |
| 2007/0117910 A1 | 5/2007 | Rexin et al. |
| 2007/0123632 A1 | 5/2007 | Rexin et al. |

FOREIGN PATENT DOCUMENTS

| | | |
|---|---|---|
| EP | 0818508 | 1/1998 |
| EP | 1281359 | 2/2003 |
| EP | 1308478 | 5/2003 |
| EP | 1348383 | 10/2003 |
| EP | 1788026 | 5/2007 |
| FR | 2643905 | 9/1990 |
| FR | 2847453 | 5/2004 |
| JP | 05-310921 | 11/1993 |
| WO | WO 9420247 | 9/1994 |
| WO | WO 9622057 | 7/1996 |
| WO | WO 2005/018891 | 3/2005 |
| WO | WO 2006/056581 | 6/2006 |

OTHER PUBLICATIONS

Bonnadier, J. B. (Solvay Advanced Polymers), "Advances in high performance plastics for medical devices," Medical Polymers 2004, Proceedings of a conference held in Dublin Nov. 15-16, 2004. Rapra Technology 2004, Paper 3; 21 pp.

Unknown Author, Solvay Advanced Polymers, "Advanced plastics for medical devices," High Performance Plastics, Apr. 2006, p. 1-3, International Newsletters Ltd., UK; 5 pp.

Unknown Author, Solvay Advanced Polymers, "New polyacrylamide offers low warpage," Plastics Technology, 52(7), Jul. 2006, p. 25, Gardner Publications Inc; 3 pp.

Unknown Author, Solvay Advanced Polymers, "Product data sheet IXEF 1022/006," May 2005, pp. 1, extracted on May 29, 2007 from Internet at URL: http://www.solvaymedical.com/pdf/IEXF1022 %200006.pdf(XP002435302); 1 pp.

Loher, U., et al., "Development of a cortical bone screw made with endless carbon fibre reinforced polyetheretherketone (CF-PEEK) by extrusion, a new method", RAPRA Abstracts, Mar. 1, 1994, vol. 31 (3), p. 70, Rapra Technology Ltd., Shrewsbury, GB (XP000431417); 1 pp.

ORTHOPEDIC TOOL MADE OF A PLASTIC MATERIAL

CROSS REFERENCE TO A RELATED APPLICATION

The present application claims priority to U.S. application Ser. No. 12/520,790 filed Jun. 22, 2009, which is the national stage application of PCT/EP2007/064426, which was filed on Dec. 21, 2007 and claims priority to U.S. Provisional Application No. 60/871,840, filed on Dec. 26, 2006, the whole content of which is herein incorporated by reference.

TECHNICAL FIELD

The objective of the present invention is to provide an orthopedic tool which provides various advantages over orthopedic tools of the prior art, without retaining their drawbacks. In particular, they are well suited for a single-use as certain orthopedic tools of the prior art made of a commodity plastic; in contrast with said orthopedic tools of the prior art, they exhibit further outstanding physical, chemical and mechanical properties. Also surprisingly, they exhibit excellent biocompatibility and are harmless for the human body, complying even with certain severe tests for food applications, including the so-known USP Class VI and WRAS BF920/NSF 51 standard tests.

With this end in view, the present invention concerns an orthopedic tool, said orthopedic tool consisting essentially of, or said orthopedic tool comprising at least one part consisting essentially of, at least one plastic material (M), wherein the plastic material (M) comprises at least one semi-aromatic polyamide (P) comprising more than 50 mole % of recurring units obtained by the polycondensation reaction between at least one aliphatic diacid or derivative thereof and at least one aromatic diamine.

In the rest of the text, the expression "part", "plastic material" and "aromatic polyamide" are understood, for the purpose of the present invention, both in the plural and the singular, that is to say that the invented orthopedic tool may comprise one or more parts, that the invented orthopedic tool and its part(s) may comprise one or more plastic materials, and that the plastic material (M) may comprise one or more semi-aromatic polyamides (P).

BACKGROUND

The Orthopedic Tool

For the purpose of the present invention, an orthopedic tool is intended to denote a tool useful for the treatment of disorders of the skeleton, articulations and/or the locomotive system (i.e. the set formed by the skeleton, the muscles attached thereto, and the part of the nervous system which controls the muscles).

Preferably above 50 wt. %, more preferably above 80 wt. % and still more preferably above 90 wt. % of the orthopedic tool is made of the plastic material (M). Most preferably, the orthopedic tool consists essentially, or even better consists of, the plastic material (M).

The orthopedic tool is preferably a tool for machining bones.

Certain orthopedic tools are described in EP 0 574 701 B1 (to Kropf), the whole content of which is herein incorporated by reference; they are tools for machining bones with a working part that comprises at least one cutting edge for abrading bones through rotation of the tool, and with an adapter intended for coupling the tool to a rotatable drive, the working part and its at least one cutting edge being made of plastic. Orthopedic tools according to the present invention include the orthopedic tools as described in EP 0 574 701 B, wherein Kropf's plastic is partly or completely replaced by the plastic material (M).

Certain other orthopedic tools are described in WO 94/20247 (to Bordes), the whole content of which is herein incorporated by reference; they are drills comprising a rod portion connectable to an apparatus such as a drilling unit as well as an operative cutting portion, said portions forming a single disposable plastic unit. Orthopedic tools according to the present invention include also the orthopedic tools as described in WO 94/20247, wherein Bordes' plastic is partly or completely replaced by the plastic material (M).

Certain instruments and ancillaries used to remove bones for hip or knee prosthetic surgery, which comprise one or more plastics, are described in US 2006/0111725 A (to Biegun), the whole content of which is herein incorporated by reference. Instruments and ancillaries according to the present invention include the instruments and ancillaries as described in US 2006/0111725 A, wherein Biegun's plastics are partly or completely replaced by the plastic material (M). Certain instruments and ancillaries as described in US 2006/0111725 A comprise one or more metal parts; these ones, while being in accordance with the present invention if they comprise the plastic material (M), are however not preferred. For convenience, the most relevant excerpts of US 2006/0111725 A, insofar as the present invention is concerned, are reproduced herebelow as such.

The abstract of US 2006/0111725 A states that: "The invention <in accordance with US 2006/0111725 A> concerns an accessory for removing material, in particular a file (3) or a cutting block, for prosthesis implantation surgery, in particular for hip or knee prostheses. The invention is characterised in that it comprises at least partly one plastic part and at least one insert (4, 10, 5) made of a material harder than the bone material, in particular of metal, which is fixed to the plastic material such that if the device is brought to a temperature Ti, the insert is separated from the plastic material."

The description of US2006111725 states notably that:

This invention <in accordance with US 2006/0111725 A> relates to instruments or ancillaries used to remove bones for hip or knee prosthetic surgery and in particular to a rasp for fitting a hip prosthesis and to a cutting unit for fitting a knee prosthesis. This invention also relates to a surgeon's ancillary kit, notably for filling a hip prosthesis comprising a rasp according to the invention and/or for fitting a knee prosthesis comprising a cutting unit according to the invention. ( . . . ).

FIG. 1 <which corresponds to FIG. 1 of the present patent title> shows a rasp according to the invention for cutting a bone to fit a hip prosthetic.

Figure 2:
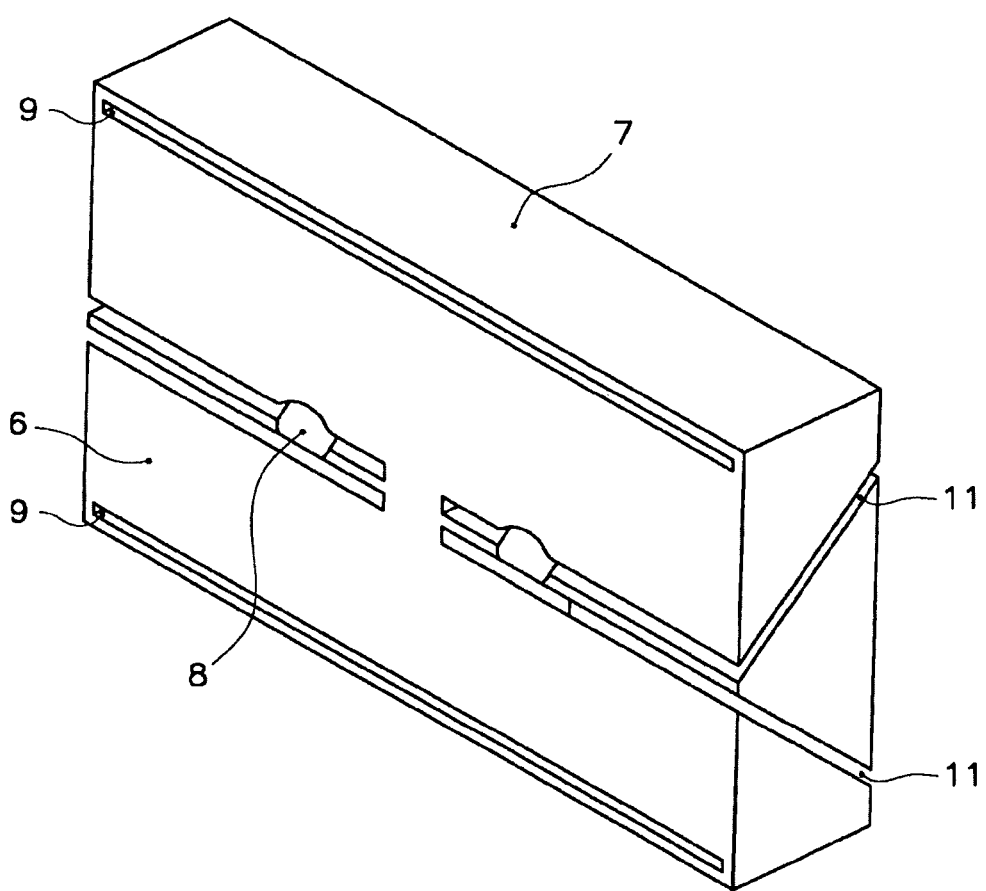

FIG. 2 <which corresponds to FIG. 2 of the present patent title> shows a cutting unit for cutting a hone of the femur or tibia.

FIG. 1 shows a rasp 1 for a hip prosthesis. It consists of a curved, cylindrical grab handle 2 and of a part 3 of a rasp spiked with protrusions for rubbing the bone to reduce it to powder.

Rasp part 3 is locked at one end of handle 2 by a locking system.

Rasp part 3 is made of plastic ( . . . ).

Handle 2 is made of plastic ( . . . ).

FIG. 2 shows a cutting unit 6 for a knee prosthesis. This unit 6 consists of a box-shaped body 7 drilled with two holes 8 for fixing by screw to the bone to be cut and comprises two horizontal slots 9 and two sloping slots 11, through which cutting blades can be inserted to resection bones for installing the prosthesis, slots 9 and/or 11 being chosen according to the angle of attack of the cut required.

The cutting unit is made of plastic ( . . . )

It is formed by injection moulding. Metal inserts with or without shape memory and at least partly embedded in the plastic mass can be used in the same way as for the rasp described above."

SUMMARY

Preferably, the orthopedic tool is chosen from instruments and ancillaries used to remove bones for hip or knee prosthetic surgery. Said instruments and ancillaries are in accordance with the present invention, as soon as they consist essentially of, or comprise at least one part consisting essentially of, at least one plastic material (M), wherein the plastic material (M) comprises at least one semi-aromatic polyamide (P) comprising more than 50 mole % of recurring units obtained by the polycondensation reaction between at least one aliphatic diacid or derivative thereof and at least one aromatic diamine. The instruments and ancillaries in accordance with the present invention are preferably essentially free (or even, completely free) of metal.

More preferably, the orthopedic tool is chosen from rasps for fitting a hip prosthesis (hereinafter, "hip rasp") and cutting units for fitting a knee prosthesis.

Still more preferably, the orthopedic tool is a hip rasp.

For the sake of clarity, the hip rasp, likewise any other orthopedic tool in accordance with the invention, consists essentially of, or comprises at least one part consisting essentially of, at least one plastic material (M), wherein the plastic material (M) comprises at least one semi-aromatic polyamide (P) comprising more than 50 mole % of recurring units obtained by the polycondensation reaction between at least one aliphatic diacid or derivative thereof and at least one aromatic diamine.

Excellent results are obtained when the hip rasp consists essentially of (or even, consists of) the plastic material (M).

DETAILED DESCRIPTION

The Semi-Aromatic Polyamide (P)

An essential feature of the present invention lies in the chemical nature of the plastic material (M), namely it comprises the semi-aromatic polyamide (P).

A polyamide is intended to denote any polymer of which more than 50 mole % of the recurring units comprise an amide moiety of formula (I):

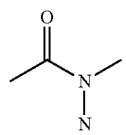

(I)

Typically, polyamides are formed by reacting a mixture comprising one or more diamine and one or more diacid monomer units, and/or by polymerizing an amino carboxylic acid or lactam.

The polyamide (P) is aromatic. An aromatic polyamide is intended to denote any polymer of which more than 50 mole % of the recurring units comprise at least one aromatic group and an amide moiety of formula (I) (aromatic recurring units, hereinafter). The aromaticity of the aromatic recurring units of an aromatic polyamide can come notably from the diacid (or derivative thereof) and/or from the diamine and/or from the aminoacid used in the polycondensation reaction. Non limitative examples of aromatic diacids are phthalic acids and naphthalenedicarboxylic acids. Metaxylylenediamine is an example of aromatic diamine.

More precisely, the polyamide (P) is semi-aromatic, that is to say that it is an aromatic polyamide as above defined which comprises recurring units derived from the polycondensation reaction between at least one non-aromatic diacid (or derivatives thereof) and an aromatic or non-aromatic diamine, and/or recurring units derived from the polycondensation reaction between an aromatic or non-aromatic diacid (or derivatives thereof) and at least one non-aromatic diamine, and/or recurring units derived from the polycondensation reaction of at least one non-aromatic aminocarboxylic acid (or derivatives thereof). A diacid (or derivative thereof) or a diamine is considered for the purpose of this invention as "aromatic" when it comprises one or more than one aromatic group. A diacid (or derivative thereof) or a diamine or an amino-carboxylic acid (or derivative thereof) is considered for the purpose of this invention as "non-aromatic" when it is free from aromatic group.

Still more precisely, the polyamide (P) is a semi-aromatic polyamide comprising recurring units derived from an aromatic diamine and an aliphatic diacid (or derivatives thereof) and/or recurring units derived from an aromatic diacid (or derivatives thereof) and an aliphatic diamine.

Still still more precisely, the polyamide (P) is a semi-aromatic polyamide comprising more than 50 mole % of recurring units obtained by the polycondensation reaction between at least one aliphatic diacid or derivative thereof and at least one aromatic diamine, preferably more than 75 mole % and more preferably more than 90 mole % of said recurring units are obtained by the polycondensation reaction between at least one aliphatic diacid or derivative thereof and at least one aromatic diamine. Still more preferably, essentially all or even all the recurring units of the semi-aromatic polyamide (P) are obtained by the polycondensation reaction between at least one aliphatic diacid or derivative thereof and at least one aromatic diamine.

The term diacid derivative is intended to encompass acid halogenides, especially chlorides, acid anhydrides, acid salts, acid amides and the like, which can be advantageously used in the polycondensation reaction.

The expression "at least one aliphatic diacid or derivative thereof" and "at least one aromatic diamine" are understood to mean that one or more than one aliphatic diacid or derivative thereof and one or more than one aromatic diamine can be made to react as above specified.

Non limitative examples of aromatic diamines are notably m-phenylene diamine (MPD), p-phenylene diamine (PPD), 3,4'-diaminodiphenyl ether (3,4'-ODA), 4,4'-diaminodiphenyl ether (4,4'-ODA), metaxylylenediamine (MXDA), as shown below:

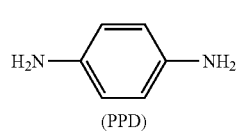
(PPD)

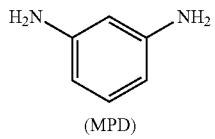
(MPD)

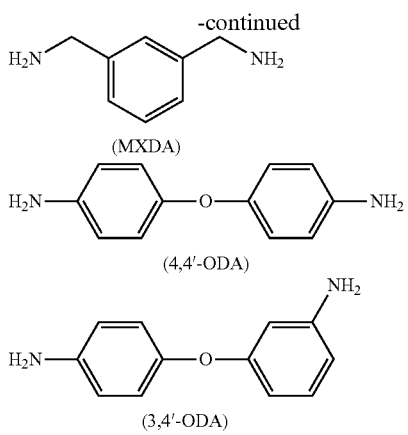

(MXDA)

(4,4'-ODA)

(3,4'-ODA)

The aromatic diamine is preferably metaxylylenediamine (MXDA).

Non limitative examples of aliphatic diacids are notably oxalic acid (HOOC—COOH), malonic acid (HOOC—CH$_2$—COOH), succinic acid [HOOC—(CH$_2$)$_2$—COOH], glutaric acid [HOOC—(CH$_2$)$_3$—COOH], 2,2-dimethyl-glutaric acid [HOOC—C(CH$_3$)$_2$—(CH$_2$)$_2$—COOH], adipic acid [HOOC—(CH$_2$)$_4$—COOH], 2,4,4-trimethyl-adipic acid [HOOC—CH(CH$_3$)—CH$_2$—C(CH$_3$)$_2$—CH$_2$—COOH], pimelic acid [HOOC—(CH$_2$)$_5$—COOH], suberic acid [HOOC—(CH$_2$)$_6$—COOH], azelaic acid [HOOC—(CH$_2$)$_7$—COOH], sebacic acid [HOOC—(CH$_2$)$_8$—COOH], undecanedioic acid [HOOC—(CH$_2$)$_9$—COOH], dodecanedioic acid [HOOC—(CH$_2$)$_{10}$—COOH], tetradecandioic acid [HOOC—(CH$_2$)$_{11}$—COOH].

The aliphatic diacid is preferably adipic acid.

As above mentioned, such aliphatic diacids can be used in the polycondensation reaction notably under the form of free acid and acid chloride.

Good results are obtained when using PMXDA polymers as the semi-aromatic polyamide (P).

For the purpose of the present invention, a PMXDA polymer is intended to denote a semi-aromatic polyamide essentially all, if not all, the recurring units of which are obtained by the polycondensation reaction of adipic acid with meta-xylylene diamine.

PMXDA polymers are notably commercially available as IXEF® polyamides from Solvay Advanced Polymers, L.L.C.

The molecular weight of the PMXDA polymer is not particularly limited. The PMXDA has advantageously a number average molecular weight (M$_n$) of at least 2,500, more preferably of at least 5,000, more preferably of at least 10,000 and still more preferably of at least 20,000. In addition, the PMXDA has advantageously a number average molecular weight (M$_n$) of at most 60,000, more preferably of at most 50,000 and still more preferably of at most 30,000.

M$_n$ can be calculated according to the following formula:

$M_n = 2 \times 10^6 / \Sigma$(—COOH end groups)+(—NH2 end groups)(—COOH end groups)=number of acid end groups in µequivalents/gram of product resin (titrated with a base)

(—NH2 end groups)=number of basic end groups in µequivalents/gram of product resin (titrated with an acid).

The semi-aromatic polyamide (P) can be amorphous or semi-crystalline. Preferably, it is semi-crystalline.

The semi-aromatic polyamide (P) is contained in the plastic material (M) in an amount of advantageously at least 10 wt. %, preferably at least 25 wt. %, more preferably at least 35 wt. % and still more preferably at least 40 wt. %, based on the total weight of the plastic material (M). Besides, the semi-aromatic polyamide (P) is contained in the plastic material (M) in an amount of advantageously at most 95 wt. %, preferably at most 80 wt. %, more preferably at most 60 wt. % and still more preferably at most 50 wt. %, based on the total weight of the plastic material (M).

Optional Ingredients of the Plastic Material (M)

Preferably, the plastic material (M) further comprises an aliphatic polyamide (P*) of which more than 50 mole % of the recurring units are obtained by the polycondensation reaction between an aliphatic diacid (and/or a derivative thereof) and an aliphatic diamine, and/or by the auto-polycondensation reaction of an amino carboxylic acid, and/or by the auto-polycondensation reaction of a lactam.

More preferably, the aliphatic polyamide (P*) is chosen from nylon 6, nylon 66 and nylon 12.

Still more preferably, the aliphatic polyamide (P*) is nylon 66, i.e. the polyamide obtained by the polycondensation reaction between 1,6-hexamethylenediamine and adipic acid.

The aliphatic polyamide (P*) is contained in the polymer composition in an amount of advantageously at least 3 wt. %, and preferably at least 6 wt. %, based on the weight of the semi-aromatic polaymide (P). Besides, the aliphatic polyamide (P*) is contained in the polymer composition in an amount of advantageously at most 30 wt. %, preferably at most 20 wt. %, and more preferably at most 15 wt. %, based on the weight of the semi-aromatic polyamide (P).

Preferably, the plastic material (M) further comprises a reinforcing fiber (F).

Any reinforcing fiber is in principle desirable. The skilled person will easily recognize the reinforcing fiber which fits best the plastic material (M) contained in the orthopedic tool. Generally, the reinforcing fiber is chosen depending on its chemical nature, its length, diameter, ability to feed nicely in compounding equipment without bridging and surface treatment (notably because good interfacial adhesion between the reinforcing fiber and the semi-aromatic polyamide (P) improves the stiffness and the toughness of the plastic material (M)).

Non limitative examples of suitable reinforcing fibers include glass fibers, asbestos, graphitic carbon fibers (some of them having possibly a graphite content of above 99%), amorphous carbon fibers, pitch-based carbon fibers, PAN-based carbon fibers, synthetic polymeric fibers, aluminum fibers, aluminum silicate fibers, oxide of metals of such aluminum fibers, titanium fibers, magnesium fibers, rock wool fibers, steel fibers, silicon carbide fibers, boron fibers and so on.

Preferably, the reinforcing fiber (F) is chosen from glass fibers and carbon fibers. More preferably, it is glass fiber.

The reinforcing fiber (F), in particular when it is glass fiber, has a diameter preferably below 40 µm: the Applicant has observed this resulted in increased reinforcement. More preferably, its diameter is below 20 µm, and still more preferably below 15 µm. On the other hand, the diameter of the reinforcing fiber, in particular the glass fiber, is preferably above 5 µm.

The reinforcing fiber (F), in particular the glass fiber, has a length preferably of below 20 mm, more preferably below 10 mm.

The reinforcing fiber (F) is contained in the polymer composition in an amount of advantageously at least 10 wt. %, preferably at least 20 wt. %, more preferably at least 30 wt. % and still more preferably at least 40 wt. %, based on the weight of the plastic material (M). Besides, the glass fiber (F) is contained in the polymer composition in an amount of advantageously at most 60 wt. %, preferably at most 55 wt. %, and more preferably at most 52 wt. %, based on the weight of the plastic material (M).

Other ingredients may be present in the plastic material (M), including pigments, lubricants and nucleating agents.

The invention claimed is:

1. An orthopedic tool comprising:
   at least one part consisting essentially of at least one plastic material (M),
   wherein the plastic material (M) includes
      at least one semi-aromatic polyamide (P) including more than 50 mole % of recurring units obtained by a polycondensation reaction between at least one aliphatic diacid or derivative thereof and at least one aromatic diamine, and
      glass fiber, in an amount of from 40 to 60 wt. %, based on a total weight of the plastic material (M), the glass fiber having a diameter ranging from 5 to 40 μm, and
   wherein the semi-aromatic polyamide (P) is contained in the plastic material (M) in an amount of from 25 to 80 wt. %, based on the total weight of the plastic material (M), and
   wherein the plastic material (M) further comprises an aliphatic polyamide (P*) selected from the group consisting of nylon 6, nylon 66 and nylon 12, in an amount of from 3 to 15 wt. %, based on a weight of the semi-aromatic polyamide (P).

2. The orthopedic tool according to claim 1, wherein the orthopedic tool is an instrument or ancillary used to remove bones for hip or knee prosthetic surgery.

3. The orthopedic tool according to claim 2, wherein the orthopedic tool is a hip rasp.

4. The orthopedic tool according to claim 1, wherein the semi-aromatic polyamide (P) is a PMXDA polymer.

5. The orthopedic tool according to claim 1, wherein the plastic material (M) further comprises a pigment.

6. The orthopedic tool according to claim 1, wherein the glass fiber has a diameter ranging from 5 to 15 μm.

* * * * *